US00PP15126P2

(12) United States Plant Patent
Sato

(10) Patent No.: US PP15,126 P2
(45) Date of Patent: Aug. 31, 2004

(54) BEGONIA PLANT NAMED 'GUM DROP WHITE'

(50) Latin Name: *Begonia semperflorens*
Varietal Denomination: Gum Drop White

(75) Inventor: Kazunori Sato, Tokyo (JP)

(73) Assignee: Bodger Seeds, Ltd., South el Monte, CA (US)

( * ) Notice: Subject to any disclaimer, the term of this patent is extended or adjusted under 35 U.S.C. 154(b) by 0 days.

(21) Appl. No.: 10/684,523

(22) Filed: Oct. 13, 2003

(51) Int. Cl.[7] ..... A01H 5/00
(52) U.S. Cl. ..... Plt./343
(58) Field of Search ..... Plt./343

*Primary Examiner*—Bruce R. Campell
*Assistant Examiner*—W C Haas
(74) *Attorney, Agent, or Firm*—C. A. Whealy

(57) ABSTRACT

A new and distinct cultivar of Begonia plant named 'Gum Drop White', characterized by its compact, upright and uniform plant habit; freely branching growth habit, dense and bushy growth habit; green-colored leaves; freely flowering habit with numerous flowers per plant; and small mostly double flowers that are white in color and held above and beyond the foliage.

1 Drawing Sheet

Botanical classification/cultivar designation: *Begonia semperflorens* cultivar Gum Drop White.

BACKGROUND OF THE INVENTION

The present Invention relates to a new and distinct cultivar of Begonia plant, botanically known as *Begonia semperflorens*, and hereinafter referred to by the name 'Gum Drop White'.

The new Begonia is a product of a planned breeding program conducted by the Inventor in Fukuoka, Kyushu, Japan. The objective of the breeding program was to develop new Begonia cultivars with double flowers and attractive leaf and flower coloration.

The new Begonia originated from a cross made by the Inventor in 1995, of the *Begonia semperflorens* cultivar Double Pink, not patented, as the female, or seed parent, with the *Begonia semperflorens* cultivar Ambassador White, not patented, as the male, or pollen parent. The cultivar Gum Drop White was discovered and selected by the Inventor as a flowering plant within the progeny of the stated cross in a controlled environment in Fukuoka, Kyushu, Japan.

Asexual reproduction of the new Begonia by cuttings taken in a controlled environment in Fukuoka, Kyushu, Japan since 1999 has shown that the unique features of this new Begonia are stable and reproduced true to type in successive generations.

SUMMARY OF THE INVENTION

The cultivar 'Gum Drop White' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gum Drop White'. These characteristics in combination distinguish 'Gum Drop White' as a new and distinct Begonia cultivar.

1. Compact, upright and uniform plant habit.
2. Freely branching growth habit, dense and bushy growth habit.
3. Green-colored leaves.
4. Freely flowering habit, numerous flowers per plant.
5. Small mostly double flowers that are white in color and held above and beyond the foliage.

Plants of the new Begonia differ from plants of the female parent, the cultivar Double Pink, in leaf and flower coloration as plants of the cultivar Double Pink have bronze-colored leaves and pink-colored flowers. Plants of the new Begonia differ from plants of the male parent, the cultivar Ambassador White, in flower form as plants of the cultivar Ambassador White have single flowers.

The new Begonia can be compared to the *Begonia semperflorens* cultivar Queen White, not patented. However, in side-by-side comparisons conducted in Fukuoka, Kyushu, Japan, plants of the new Begonia differed from plants of the cultivar Queen White in the following characteristics.

1. Plants of the new Begonia had smaller leaves than plants of the cultivar Queen White.
2. Plants of the new Begonia had smaller flowers than plants of the cultivar Queen White.
3. Flowers of plants of the new Begonia were more often double than plants of the cultivar Queen White.
4. Flowers of plants of the new Begonia did not produce pollen whereas flowers of plants of the cultivar Queen White produced pollen.

BRIEF DESCRIPTION OF THE PHOTOGRAPHS

The accompanying colored photographs illustrate the overall appearance of the new Begonia, showing the colors as true as it is reasonably possible to obtain in colored reproductions of this type. Colors in the photographs may differ slightly from the color values cited in the detailed botanical description which accurately describe the colors of the new Begonia.

The photograph at the top of the sheet comprises a side perspective view of a typical flowering plant of 'Gum Drop White'.

The photograph at the bottom of the sheet is a close-up view of typical flowers and leaves of 'Gum Drop White'.

DETAILED BOTANICAL DESCRIPTION

In the following description, color references are made to The Royal Horticultural Society Colour Chart, 1995 Edition, except where general items of ordinary dictionary significance are used. The aforementioned photographs and following observations and measurements describe plants grown in Lompoc, Calif. under commercial practice during the summer and fall in a polycarbonate-covered greenhouse with day temperatures about 21 to 27° C., night temperatures about 16 to 18° C. and light levels about 4,000 to 8,000 foot-candles. Unrooted cuttings were directly planted in 10-cm containers and grown for about seven weeks.

Botanical classification: *Begonia semperflorens* cultivar Gum Drop White.

Parentage:

*Female, or seed, parent.*—*Begonia semperflorens* cultivar Double Pink, not patented.

*Male, or pollen, parent.*—*Begonia semperflorens* cultivar Ambassador White, not patented.

Propagation:

*Type.*—Top cuttings.

*Time to initiate roots, summer.*—About 17 days at temperatures of 25° C.

*Time to initiate roots, winter.*—About 21 days at temperatures of 23° C.

*Time to develop roots, summer.*—About 25 days at temperatures of 25° C.

*Time to develop roots, winter.*—About 32 days at temperatures of 23° C.

*Root description.*—Fibrous, fleshy, fine.

Plant description:

*Plant form.*—Compact, upright and uniform plant habit; mounded inverted triangle; freely branching with about six to seven lateral branches per plant; dense and bushy growth habit. Flowers are mostly double and abundant.

*Growth habit.*—Moderate growth rate, vigorous. Suitable for 10 to 15-cm containers.

*Plant height.*—About 20 cm.

*Plant width.*—About 22 cm.

*Lateral branches.*—Length: About 18 cm. Diameter: About 6 mm. Internode length: About 3.75 cm. Orientation: Mostly upright. Strength: Very strong. Texture: Smooth, glabrous. Color: 144B.

*Leaves.*—Arrangement: Simple, alternate. Length: About 6.5 cm. Width: About 6 cm. Shape: Ovate to reniform. Apex: Broadly acute. Base: Somewhat cordate to oblique. Margin: Very slightly serrate. Texture, upper and lower surfaces: Smooth, glabrous; waxy. Venation pattern: Palmate. Color: Developing leaves, upper and lower surfaces: 144A. Fully expanded leaves, upper surface: 146A. Fully expanded leaves, lower surface: 147B. Venation, upper and lower surfaces: 146B. Petiole length: About 1.5 cm. Petiole diameter: About 4 mm. Petiole texture, upper and lower surfaces: Smooth, glabrous. Petiole color, upper and lower surfaces: 144C.

Flower description:

*Flowering habit.*—Mostly double flowers with numerous tepals arranged in axillary cymes. Freely flowering habit with typically five to six flowers per cyme. Many cymes in flower simultaneously. Flowers positioned above and beyond the foliage. Flowers not fragrant. Flowers not persistent.

*Natural flowering season.*—Plants of the new Begonia flower year around; flowering continuous.

*Flower longevity.*—Flowers last about ten days on the plant.

*Cyme height.*—About 4.5 cm.

*Cyme diameter.*—About 7 cm.

*Flowers.*—Shape: Oval to rounded. Diameter: About 3 by 3.5 cm. Depth (height): About 3 cm.

*Flower buds.*—Length: About 1.2 cm. Diameter: About 1.8 cm. Shape: Oval to reniform. Color: 155A.

*Tepals.*—Arrangement: Rosette. Quantity per flower: More than 50 per flower. Shape: Obovate. Apex: Obtuse. Margin: Entire to sinuate. Length, outer tepals: About 1.5 cm. Width, outer tepals: About 1 cm. Texture, upper and lower surfaces: Smooth, glabrous; velvety. Color: When opening, upper and lower surfaces: 155A. Fully opened, upper and lower surfaces: 155D.

*Flower bracts.*—Arrangement: Two, opposite. Length: About 1.5 cm. Width: About 2 cm. Shape: Reniform. Apex: Rounded. Margin: Entire. Texture, upper and lower surfaces: Smooth, glabrous. Color, upper surface: 155A. Color, lower surface: 155D.

*Peduncles.*—Length: About 5 cm. Diameter: About 2 mm. Strength: Strong. Texture: Smooth, glabrous. Color: 144D.

*Pedicels.*—Length: About 1.2 cm. Diameter: About 1 mm. Strength: Strong, but flexible with weight of flowers. Texture: Smooth, glabrous. Color: 155D.

*Reproductive organs.*—Stamens: None observed. Pistils: Occasionally observed on individual (non-double) flowers. Pistil length: About 1.5 cm. Style length: About 4 mm. Style color: 155D. Stigma color: 12A. Ovary color: 145B.

*Seed/fruit.*—Seed and fruit production has not been observed as reproductive organs are not formed.

Disease/pest resistance: Plants of new the Begonia have not been observed to be resistant to pathogens and pests common to Begonias.

It is claimed:

1. A new and distinct cultivar of Begonia plant named 'Gum Drop White', as illustrated and described.

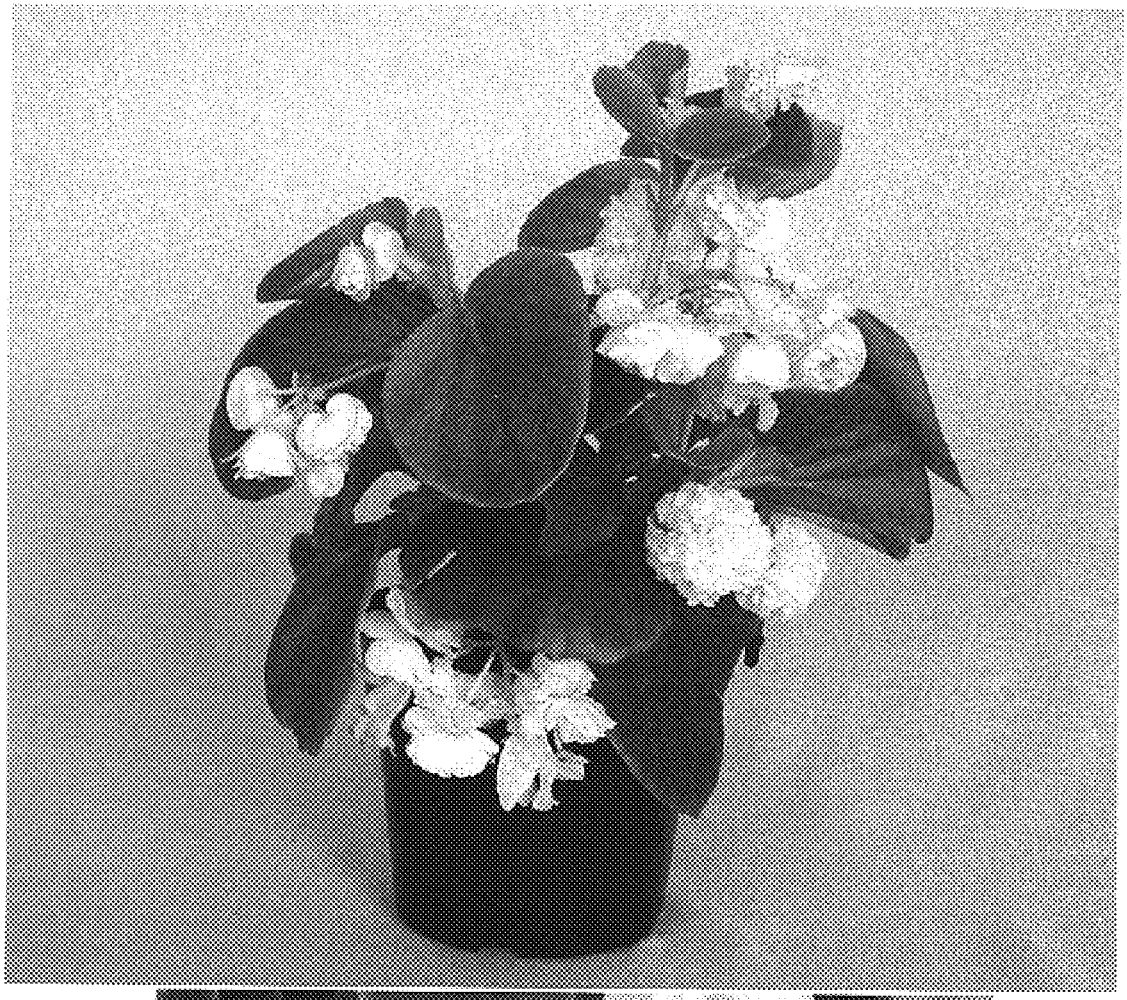
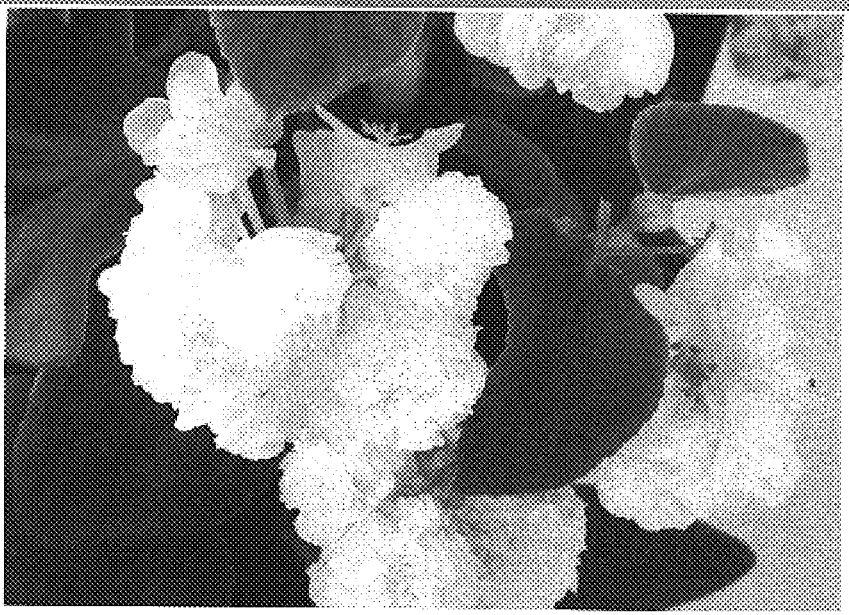

* * * * *